United States Patent
Mckinley et al.

(10) Patent No.: US 8,834,358 B2
(45) Date of Patent: Sep. 16, 2014

(54) CANNULA WITH INTEGRATED CAMERA AND ILLUMINATION

(71) Applicant: EndoSphere Surgical, Inc., Newton, MA (US)

(72) Inventors: Arthur C. Mckinley, Westport, MA (US); Jesse R. Plouffe, Wilmington, MA (US); Melvin B. Prenovitz, Newton, MA (US); Stephen J. Herman, Andover, MA (US); Vivek Sikri, Cambridge, MA (US)

(73) Assignee: EndoSphere Surgical, Inc., Newton, MA (US)

( * ) Notice: Subject to any disclaimer, the term of this patent is extended or adjusted under 35 U.S.C. 154(b) by 0 days.

(21) Appl. No.: 13/835,818

(22) Filed: Mar. 15, 2013

(65) Prior Publication Data

US 2014/0107417 A1 Apr. 17, 2014

Related U.S. Application Data

(63) Continuation-in-part of application No. 12/748,062, filed on Mar. 26, 2010, now Pat. No. 8,439,830.

(60) Provisional application No. 61/261,910, filed on Nov. 17, 2009, provisional application No. 61/164,215, filed on Mar. 27, 2009.

(51) Int. Cl.
| | |
|---|---|
| *A61B 1/05* | (2006.01) |
| *A61B 1/00* | (2006.01) |
| *A61B 1/018* | (2006.01) |
| *A61B 1/06* | (2006.01) |
| *A61B 1/12* | (2006.01) |
| *A61B 17/34* | (2006.01) |
| *A61B 19/00* | (2006.01) |

(52) U.S. Cl.
CPC ......... *A61B 1/00096* (2013.01); *A61B 1/00087* (2013.01); *A61B 1/018* (2013.01);
(Continued)

(58) Field of Classification Search
CPC ........... A61B 1/00101; A61B 1/00183; A61B 1/0008; A61B 1/053; A61B 1/0676
USPC ......... 600/109, 111, 129, 128, 154, 157, 166, 600/173, 175, 179, 117; 348/45, 65
See application file for complete search history.

(56) References Cited

U.S. PATENT DOCUMENTS

| | | | | | |
|---|---|---|---|---|---|
| 4,488,039 | A | * | 12/1984 | Sato et al. | 250/216 |
| 4,779,130 | A | * | 10/1988 | Yabe | 348/76 |

(Continued)

FOREIGN PATENT DOCUMENTS

EP 0556056 A1 8/1993

OTHER PUBLICATIONS

Cadeddu, J. et al., "Novel magnetically guided intra-abdominal camera to facilitate laparoendoscopic single-site surgery: initial human experience," Surg. Endosc., (Aug. 2009), .23: 1894-1899, (Published online May 9, 2009).

(Continued)

*Primary Examiner* — John P Leubecker
(74) *Attorney, Agent, or Firm* — Goodwin Procter LLP

(57) ABSTRACT

A cannula assembly includes a tubular element forming a lumen, a deployable element of a subassembly, and an electronic component mounted to the deployable element. The tubular element has a proximal end and a distal end adapted to be inserted into a body cavity. The deployable element is coupled through the subassembly to the tubular element, and is adapted to transition between a closed position and an open position. The electronic component has at least one imaging device and at least one illumination source. The subassembly, including the deployable element and the electronic component, are releasable from the tubular element.

23 Claims, 16 Drawing Sheets

(52) U.S. Cl.
CPC ..... *A61B 2017/3454* (2013.01); *A61B 17/3496* (2013.01); *A61B 19/5212* (2013.01); *A61B 2017/346* (2013.01); *A61B 17/3421* (2013.01); *A61B 2017/3445* (2013.01); *A61B 1/0676* (2013.01); *A61B 1/00009* (2013.01); *A61B 1/126* (2013.01); *A61B 1/05* (2013.01); *A61B 19/5202* (2013.01)
USPC ............ 600/173; 600/117; 600/129; 600/179

(56) References Cited

U.S. PATENT DOCUMENTS

| | | | |
|---|---|---|---|
| 4,788,967 A * | 12/1988 | Ueda | 600/129 |
| 4,858,001 A | 8/1989 | Milbank et al. | |
| 5,166,787 A | 11/1992 | Irion | |
| 5,167,221 A | 12/1992 | Chikama | |
| 5,183,471 A | 2/1993 | Wilk | |
| 5,256,149 A | 10/1993 | Banik et al. | |
| 5,305,121 A | 4/1994 | Moll | |
| 5,381,784 A | 1/1995 | Adair | |
| 5,443,484 A | 8/1995 | Kirsch et al. | |
| 5,448,990 A | 9/1995 | De Faria-Correa | |
| 5,506,912 A * | 4/1996 | Nagasaki et al. | 382/103 |
| 5,518,502 A * | 5/1996 | Kaplan et al. | 600/157 |
| 5,538,497 A | 7/1996 | Hori | |
| 5,569,160 A | 10/1996 | Sauer et al. | |
| 5,588,949 A | 12/1996 | Taylor et al. | |
| 5,630,795 A * | 5/1997 | Kuramoto et al. | 604/30 |
| 5,653,677 A | 8/1997 | Okada et al. | |
| 5,720,761 A | 2/1998 | Kaali | |
| 5,791,231 A | 8/1998 | Cohn et al. | |
| 5,797,943 A | 8/1998 | Danks et al. | |
| 5,860,996 A | 1/1999 | Urban et al. | |
| 5,891,013 A | 4/1999 | Thompson | |
| 5,899,851 A | 5/1999 | Koninckx | |
| 5,957,832 A | 9/1999 | Taylor et al. | |
| 6,097,423 A | 8/2000 | Mattsson-Boze et al. | |
| 6,348,034 B1 | 2/2002 | Thompson | |
| 6,371,909 B1 | 4/2002 | Hoeg et al. | |
| 6,387,043 B1 | 5/2002 | Yoon | |
| 6,478,730 B1 | 11/2002 | Bala et al. | |
| 6,508,759 B1 | 1/2003 | Taylor et al. | |
| 6,527,704 B1 | 3/2003 | Chang et al. | |
| 6,648,816 B2 | 11/2003 | Irion et al. | |
| 6,767,321 B2 | 7/2004 | Czarnek et al. | |
| 6,863,651 B2 | 3/2005 | Remijan et al. | |
| 6,916,286 B2 | 7/2005 | Kazakevich | |
| 6,984,203 B2 | 1/2006 | Tartaglia et al. | |
| 6,984,205 B2 * | 1/2006 | Gazdzinski | 600/160 |
| 6,986,738 B2 | 1/2006 | Glukhovsky et al. | |
| 7,037,258 B2 | 5/2006 | Chatenever et al. | |
| 7,041,052 B2 | 5/2006 | Saadat et al. | |
| 7,066,879 B2 | 6/2006 | Fowler et al. | |
| 7,211,042 B2 * | 5/2007 | Chatenever | 600/117 |
| 7,322,934 B2 | 1/2008 | Miyake et al. | |
| 7,585,273 B2 | 9/2009 | Adler et al. | |
| 7,604,648 B2 | 10/2009 | Kerr | |
| 7,927,272 B2 | 4/2011 | Bayer et al. | |
| 7,967,744 B2 * | 6/2011 | Kaye et al. | 600/154 |
| 8,083,667 B2 | 12/2011 | Cooper et al. | |
| 8,105,233 B2 | 1/2012 | Abou El Kheir | |
| 2002/0049367 A1 | 4/2002 | Irion et al. | |
| 2003/0055319 A1 | 3/2003 | Chang | |
| 2003/0236505 A1 | 12/2003 | Bonadio et al. | |
| 2005/0029978 A1 | 2/2005 | Oleynikov et al. | |
| 2005/0038317 A1 * | 2/2005 | Ratnakar | 600/101 |
| 2005/0059862 A1 | 3/2005 | Phan | |
| 2005/0085691 A1 | 4/2005 | Nakao | |
| 2005/0154256 A1 | 7/2005 | Breidenthal et al. | |
| 2005/0182293 A1 | 8/2005 | Katzman | |
| 2005/0234296 A1 | 10/2005 | Saadat et al. | |
| 2006/0069314 A1 | 3/2006 | Farr | |
| 2006/0106286 A1 | 5/2006 | Wendlandt et al. | |
| 2006/0183095 A1 | 8/2006 | Korndorffer et al. | |
| 2006/0252994 A1 | 11/2006 | Ratnakar | |
| 2007/0032701 A1 | 2/2007 | Fowler et al. | |
| 2007/0073109 A1 | 3/2007 | Irion | |
| 2007/0093812 A1 | 4/2007 | Hayashida et al. | |
| 2007/0179430 A1 | 8/2007 | Smith et al. | |
| 2007/0249899 A1 | 10/2007 | Seifert | |
| 2008/0027279 A1 | 1/2008 | Abou El Kheir | |
| 2008/0065099 A1 | 3/2008 | Cooper et al. | |
| 2008/0147018 A1 | 6/2008 | Squilla et al. | |
| 2008/0208006 A1 | 8/2008 | Farr | |
| 2008/0269557 A1 | 10/2008 | Marescaux et al. | |
| 2008/0269562 A1 | 10/2008 | Marescaux et al. | |
| 2009/0012530 A1 | 1/2009 | Fowler | |
| 2009/0018400 A1 | 1/2009 | Raymond et al. | |
| 2009/0036744 A1 | 2/2009 | Vayser | |
| 2009/0259097 A1 | 10/2009 | Thompson | |
| 2009/0259102 A1 | 10/2009 | Koninckx et al. | |
| 2009/0275799 A1 | 11/2009 | Saadat et al. | |
| 2009/0312773 A1 | 12/2009 | Cabrera et al. | |
| 2010/0010504 A1 | 1/2010 | Simaan et al. | |
| 2010/0081875 A1 | 4/2010 | Fowler et al. | |
| 2010/0185197 A1 | 7/2010 | Sakao et al. | |
| 2010/0280316 A1 | 11/2010 | Dietz et al. | |
| 2011/0230894 A1 * | 9/2011 | Simaan et al. | 606/130 |
| 2012/0310044 A1 * | 12/2012 | Wendlandt et al. | 600/109 |

OTHER PUBLICATIONS

Fowler, D.L. et al., "Initial trial of a stereoscopic, insertable, remotely controlled camera for minimal access surgery," Surg. Endosc. (Jan. 2010), 24:9-15, (Published online Jun. 11, 2009).

International Search Report and Written Opinion for International Application No. PCT/US2010/028881 mailed on Oct. 29, 2010.

Karl Storz Full HD, "Optimized workflow," www.karlstorz-hd-endoscopy.com, (accessed Jan. 27, 2011), 1 page.

* cited by examiner

CANNULA WITH INTEGRATED CAMERA AND ILLUMINATION

CROSS-REFERENCE TO RELATED APPLICATIONS

This application is a continuation-in-part of U.S. patent application Ser. No. 12/748,062, now U.S. Pat. No. 8,439,830, titled "Cannula with Integrated Camera and Illumination," filed on Mar. 26, 2010, which claims priority to and the benefit of U.S. Provisional Patent Application Ser. No. 61/164,215, titled "Cannula with Embedded Camera and Illumination," filed on Mar. 27, 2009, and U.S. Provisional Patent Application Ser. No. 61/261,910, titled "Shape Memory Alloy Group, Applications Including SMA Clips, Closures and Endoscope Steering," filed on Nov. 17, 2009. Disclosures of all of these applications are hereby incorporated herein by reference in their entireties.

TECHNICAL FIELD

The present invention relates generally to cannulas with integrated imaging and illumination devices and, more particularly, to those configured with a deployable portion.

BACKGROUND

In minimally invasive surgery, there are often several small incisions made into the body to insert surgical tools, insufflation devices, endoscopes, or other viewing devices. Surgeons are now performing procedures in a manner that minimizes the number of incisions, possibly to only one, referred to as Single Port Incision or Single Port Access (SPA). Surgeons are also using natural orifices, such as the mouth, to provide access for procedures using no incision or only incisions internal to the body.

The advantages sought by surgeons by reducing the number of incision points to as few as possible are to lessen trauma to the patient, reduce the incidence of infection, improve recovery time, and decrease cosmetic damage.

The reduction of incision locations will change how surgeons and their teams work. There may no longer be room around the access point to accommodate multiple surgeons who would normally hold and adjust instruments around the surgical field. A single surgeon may need to control all of the instruments for the procedure through one access point.

For example, endoscopic surgical procedures performed through a tubular cannula have evolved over the years. Presently, surgeons are performing endoscopic procedures in any hollow viscus of the torso body area after the region is insufflated. Typically, multiple narrow cannulas are each inserted through individual small entrance wounds (i.e., ports) in the skin, in order to accommodate various instruments, as well as varying viewing angles. To accomplish their insertion, separate trocars are used in conjunction with the cannulas to puncture the body cavity. A trocar is a guide placed inside the cannula with either a pointed cutting blade or blunt tip, depending on whether it is used to puncture the skin or enter through a separately made incision. Once the cannula is inserted, the trocar is removed, leaving the hollow cannula in place for use during the procedure.

The entry and deployment of imaging and/or lighting components can aid surgical procedures, such as endoscopic procedures. Examples of tubular cannula with deployable imaging and/or lighting components are described in U.S. Pat. No. 5,166,787 to Irion, U.S. Application Publication No. 2009/0275799 to Saadat et al., U.S. Application Publication No. 2009/0259097 to Thompson, and U.S. Application Publication. No. 2008/0065099 to Cooper et al., the disclosures of all of which are herein incorporated by reference in their entireties.

There is, therefore, a need in the art for a surgical apparatus assembly combining trocar cannula, with imaging and illumination capabilities, in order to minimize the number of openings in the body per procedure.

SUMMARY OF THE INVENTION

Prior art surgical instruments lack the ability to protect the optics of both imagers and illumination during insertion and removal and lack the ability to obtain a viewing angle that is offset from the cannula axis. One purpose of the present invention is to make it easier to control the access, imaging, and instrument use during minimally invasive surgery, when using fewer incisions than typically necessary. By combining the cannula, imaging, and illumination, a single device can take the place of several, thereby allowing more efficient and more easily controlled access.

In one embodiment of the invention, a surgical apparatus includes combinations of trocar, cannula, and imaging and illumination components. In this embodiment, such combinations provide the surgeon with improved viewing of the surgical cavity. Alternative embodiments allow for reduced number of incisions on a patient.

The apparatus also allows for the development of improved surgical methods including reduced number of incisions, improved imaging of the surgical cavity, and/or improved performance of surgical effectiveness.

In one aspect, the invention relates to a cannula assembly having a tubular element forming a first lumen. The tubular element has a proximal end and a distal end adapted to be inserted into a body cavity. The cannula assembly also includes a subassembly releasably attached to the tubular element. The subassembly has a deployable element located near the distal end of the tubular element. The deployable element is adapted for movement between a closed position which substantially obstructs the first lumen and an open position which does not substantially obstruct the first lumen, and remains connected to the tubular element in the closed and open positions. The assembly also includes an electronic component coupled to the deployable element having at least one imaging device and at least one illumination source. The subassembly, including the deployable element and the electronic component, are releasable from the tubular element.

In an embodiment of the foregoing aspect, the tubular element has a proximal sealing element adapted to maintain a fluid seal within the first lumen. The cannula assembly may also have a second lumen adapted for the passage of fluids, which may be located within the tubular element. In some embodiments, a movable tube with a flexible distal end is placed within the second lumen. In other embodiments, a movable tube with an occluded distal tip forming at least one side aperture is located within the second lumen. The subassembly may be designed to be cleaned, sterilized, and reused. The electronic component may also have a heat source, which can be an electric resistive heating element and/or an emitter of electromagnetic energy. In some embodiments, at least one of the imaging device and the illumination source can be operated in the closed position. In some embodiments, at least one of the imaging device and the illumination source can be operated in the open position.

In certain embodiments, at least one of the subassembly and the tubular element has at least one multi-axis accelerometer. The cannula assembly may have an ancillary electronics module with a processor for generating images with a selectable horizon based on inputs from the multi-axis accelerometer and the imaging device. The cannula assembly may have at least two multi-axis accelerometers and use the ancillary electronics module to determine an angle of deployment of the deployable element with respect to the tubular element based on inputs from the multi-axis accelerometers.

In some embodiments, the deployable element has a hinge. The hinge can be used for movement from the open position to the closed position when the cannula assembly is being removed from a body in the open position, and can be used to maintain the deployable element in a defined position. In certain embodiments the deployable element has a movable element adapted to selectively cover the imaging device and/or the illumination source. A linkage may be coupled to the movable element to control movement thereof. The movable element may be transparent to visible light. In another embodiment, the assembly has a controllable locking mechanism used to maintain positioning of a tool disposed within the first lumen. The assembly may also include a light guide for directing illumination from the illumination source. In some embodiments, the imaging device can move relative to the deployable element.

In another aspect, the invention relates to a method of using a cannula assembly. The method includes inserting a tubular element with a first lumen, a proximal end, and a distal end and a subassembly releasably attached to the tubular element into a body cavity. The method also includes actuating a deployable element of the subassembly from a closed position substantially obstructing the lumen to an open position. An electronic component mounted to the deployable portion has at least one imaging device for providing a forward view during insertion. Further steps include inserting an instrument into the lumen for performing a surgical procedure and removing the tubular element and the subassembly from the body cavity.

In one embodiment, the method includes locking the instrument in the lumen. The electronic component may have at least one radially facing imaging device and at least one radially facing illumination source. In some embodiments, the method includes receiving an input from at least one multi-axis accelerometer and at least one imaging device and processing the input with an ancillary electronics module to generate an image with a selectable horizon. In other embodiments, the method includes receiving an input from at least two multi-axis accelerometers and processing the inputs with an ancillary electronics module to determine an angle of deployment of the deployable element with respect to the tubular element. The method may also include separating the tubular element from the subassembly and releasably attaching a new tubular element to the subassembly.

BRIEF DESCRIPTION OF THE DRAWINGS

Other features and advantages of the present invention, as well as the invention itself, can be more fully understood from the following description of the various embodiments, when read together with the accompanying drawings, in which.

DETAILED DESCRIPTION

To provide an overall understanding of the invention, certain illustrative embodiments will now be described, including apparatus and methods for displaying images. However, it will be understood by one of ordinary skill in the art that the systems and methods described herein may be adapted and modified as is appropriate for the application being addressed and that the systems and methods described herein may be employed in other suitable applications. All such adaptations and modifications are to be considered within the scope of the invention.

Figure 1:
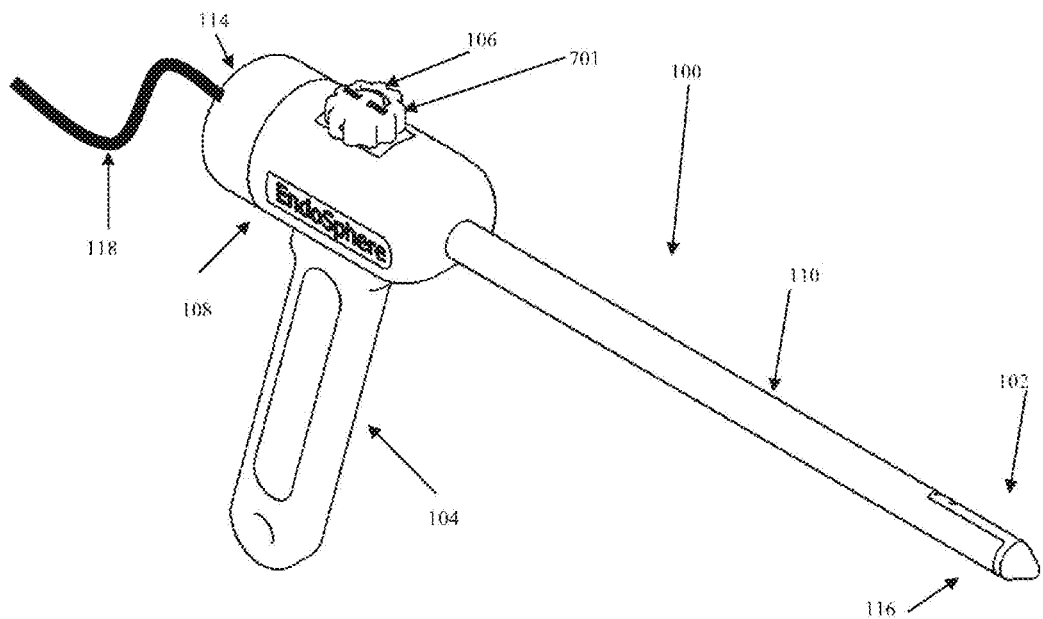
FIG. 1 depicts a schematic perspective view of a cannula assembly in a closed position, according to an embodiment of the present invention.
Figure 2:
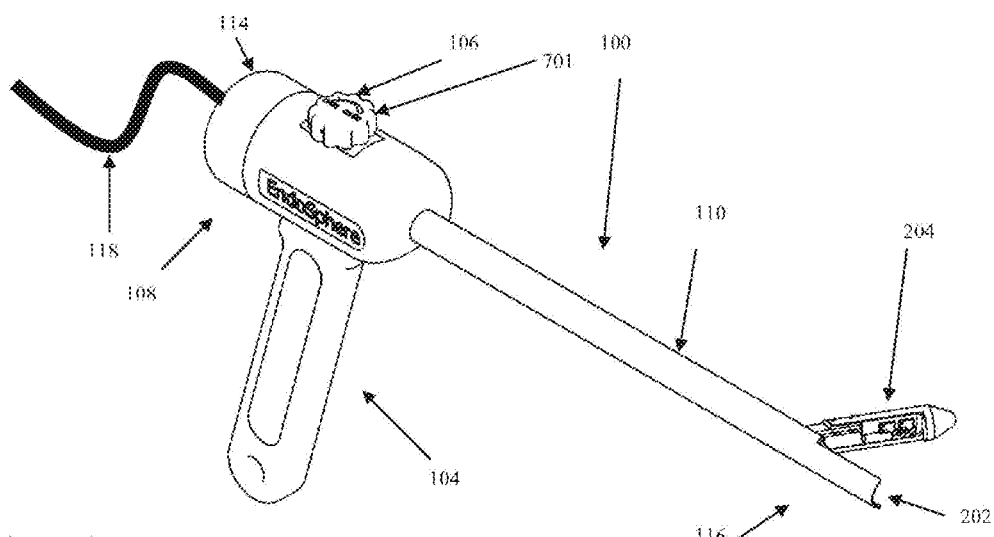
FIG. 2 depicts a schematic perspective view of the cannula assembly of FIG. 1 in one of its open positions.

FIGS. 1 and 2 depict schematic perspective views of an embodiment of the cannula assembly 100 in closed and open positions, respectively. In one embodiment, the cannula assembly 100 includes a tubular element 110 forming a lumen 202. A proximal end 114 of the tubular element 110 can be adapted for manipulation by the surgeon or clinician, and a distal end 116 can be adapted for insertion into a body cavity. A housing 108 with a handle 104 can be attached near or at the proximal end 114 for manipulation by the surgeon or clinician. In alternative embodiments, the tubular element 110 can form a variety of cross-sectional shapes, e.g., generally round or cylindrical, ellipsoidal, triangular, square, rectangular, and D-shaped (in which one side is flat).

All or parts of the distal end of the cannula assembly 100 are capable of being positioned into a closed position 102 for insertion and extraction either directly into the body cavity or through another insufflating cannula. When closed, the distal end assembly forms a pointed tip, such as a trocar capable of puncturing the patient's skin. In another embodiment, the lumen 202 of the tubular element 110 is can be fitted with a retractable and/or removable trocar, such as that depicted in FIGS. 9A-9C and described further hereinbelow. In one embodiment, the trocar is made of solid, non-transparent material; whereas, in another embodiment all or parts of the trocar are made of optically transparent or optically transmissive material.

Figure 3:
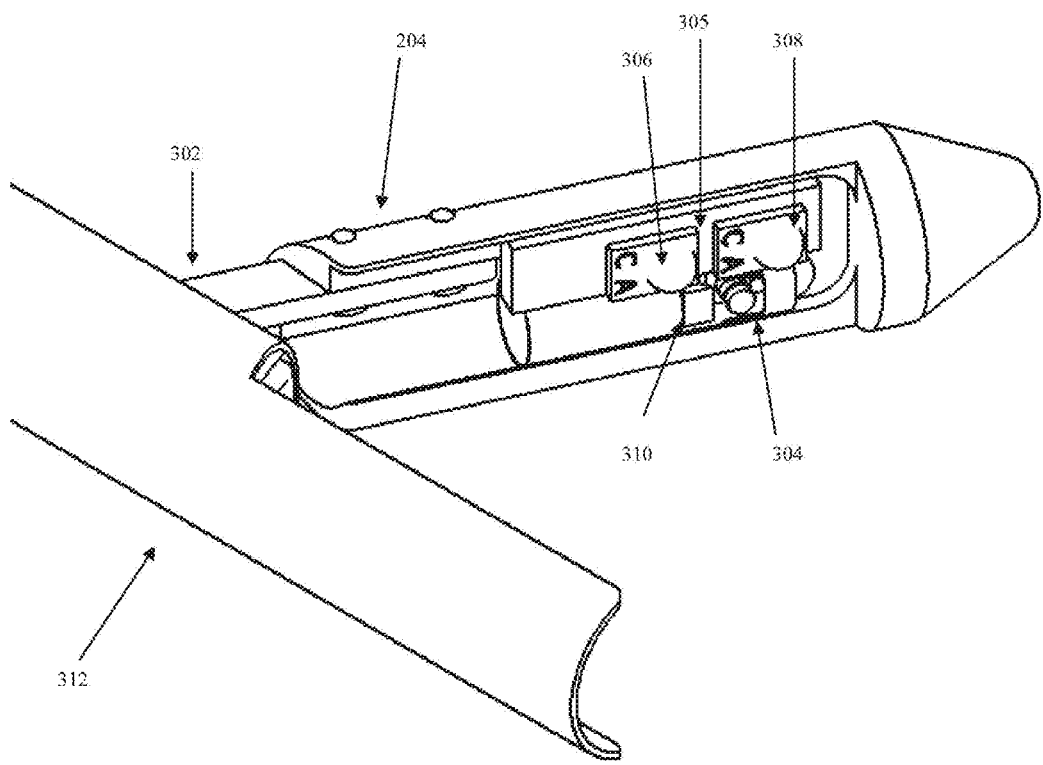
FIG. 3 depicts a close-up schematic perspective view of a tip section of the cannula assembly of FIG. 2.

One or more portions of the distal end 116 of the tubular element 110 may be designed to open once inserted into the body cavity. In one embodiment, as depicted in FIG. 3, at least one deployable portion 204 of the tubular element 110 has an adjustable angle of deployment based on the operation of the opening adjustment means 106, i.e., an actuation mechanism. For example, the adjustment means 106 can move the deployable portion 204 between a closed position and an open position. Alternatively, the adjustment means 106 can incrementally move the deployable portion 204 between a closed position and any number of open positions. In additional or alternative embodiments, the deployable portion 204 houses an electronic component, which is at least partially disposed in the lumen when in the closed position. In an alternative embodiment, all electronic components are housed within the walls of the tubular element. When the deployable portion 204 is moved to at least one open position, the lumen 202 is substantially free from obstruction due to the electronic components being moved out of the lumen, such that various instruments, e.g., surgical tools or other electronic components, can be passed through the lumen and used during the operation or surgical procedure.

The electronics components include one or more image transmission components 304, in combination with one or more illumination components 305. In one embodiment, the image transmission component 304 may be a charge-coupled device (CCD) camera, a complementary metal oxide semiconductor (CMOS) imaging device, and/or an imaging fiber optic cable, and their ancillary optics and electronic drivers for power, communication and other functions.

Optically, one or more of the image transmission components 304 may also image across the spectrum, including those portions invisible to the human eye, such as infrared and ultra-violet. In one embodiment, two image transmission components may be configured to capture stereoscopic images (in still and/or in motion). In one embodiment, one or more of the image transmission components 304 may be configured with any of a combination of fixed optics, adaptive optics, and/or active optics. Adaptive and active optics can be capable of focusing and/or zooming onto the image or target area.

In one embodiment, the one or more image transmission components 304 are capable of capturing both motion and still images, and transmitting them to the surgeon or operator through wired or wireless communication means 118 housed within or connected to the housing 108, handle 104, lumen 202 and/or the tubular element 110 wall. Such communications means 118 may include electrical signals, such as analog and/or digital, or a fiber optic communication system.

The illumination component 305 may be one or more light or illumination sources 306, 308, and their ancillary electronic drivers 310. In one embodiment, the illumination sources 306, 308 are Light Emitting Diodes (LED), organic LED (OLED), illumination fiber optic, filament lamps, electroluminescent and/or laser sources. In one embodiment, the illumination component 305 is tailored to work closely in both optical and spectrum characteristics with the image transmission component 304, with the illumination area, level, and homogeneity being optimized. In one example, this may mean the illumination level is controlled by the surgeon or clinician; whereas, in another the image transmission component Automated Gain Control (AGC) is correlated with the illumination level of the illumination component 305.

Figure 7A:
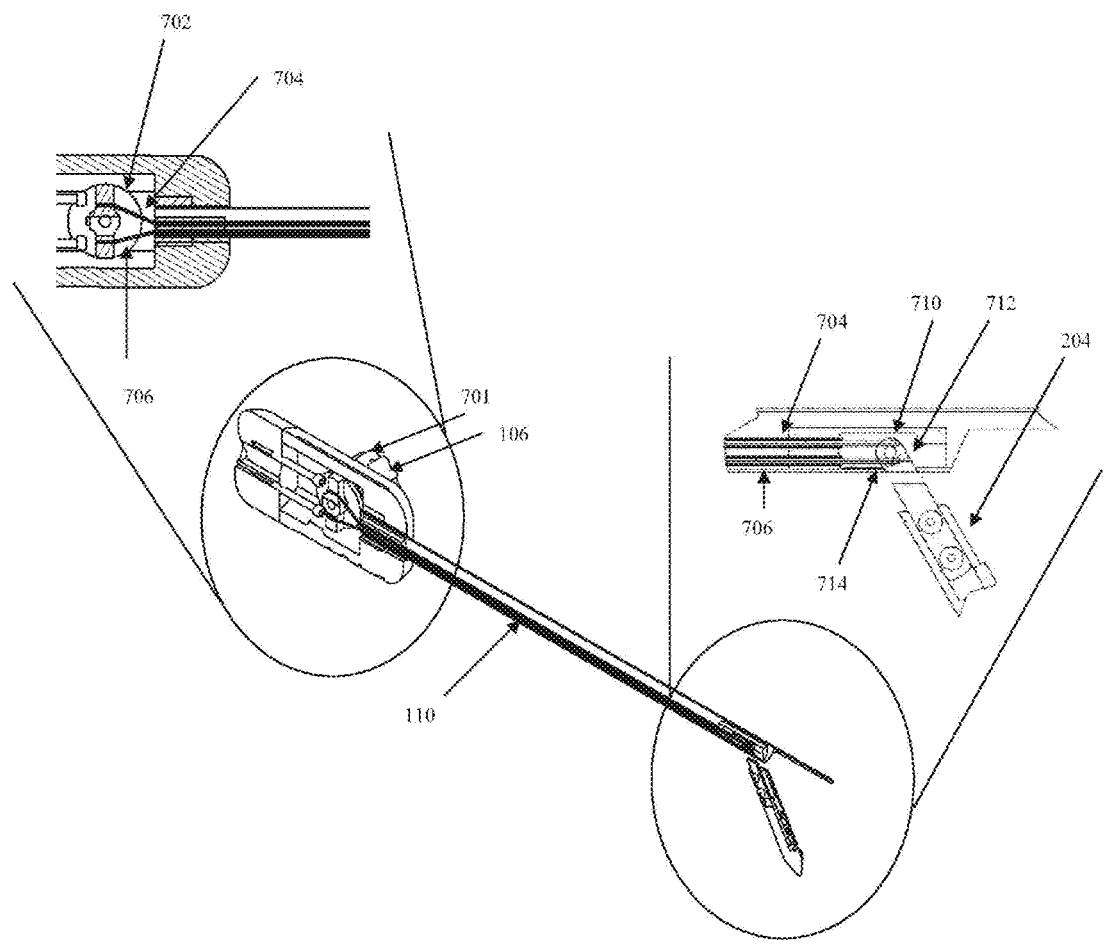
FIGS. 7A and 7B depict schematic cross-sectional close-up and schematic perspective views of an actuating mechanism connected to a deployable portion of a cannula assembly in the open and closed positions, in accordance with an embodiment of the present invention.
Figure 7B:
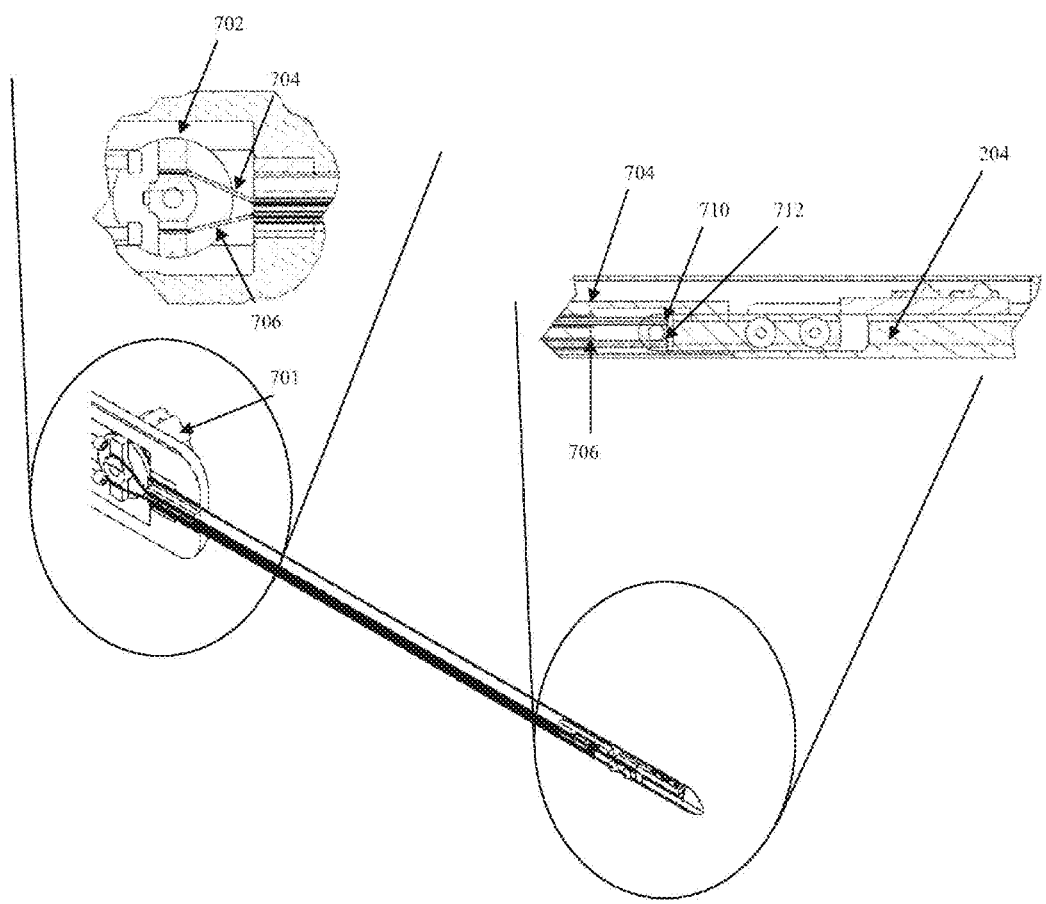

In one embodiment, as depicted in FIGS. 7A and 7B, the adjustment means 106 may include a knob 701, which is connected to a rotational wheel 702, and links 704, 706 traveling through the lumen, along the length of the tubular element 110. In an alternative embodiment, a push rod can be used in lieu of a knob 701. In another alternative embodiment, the links 704, 706 travel through one or more longitudinal apertures formed in the wall of the tubular element 110. Turning the knob 701 causes rotation of the wheel 702 in one direction, which pulls on one end of the link 706 and transfers force to its other end, which is connected to a downstream portion 712 of a hinge 714, and opens the deployable portion 204. A partial turn of the knob 701 can, for example, move the deployable portion 204 into any intermediate open position. An equivalent, but opposite turn of the knob 701 pulls on link 704, which is connected to an upstream portion 710 of the hinge 714, and closes the deployable portion 204. The links 704 may be stiff or flexible elements, such as bars, rods, cables, wires, etc. Alternatively, a nut and lead screw combination may be used. Instead of the knob 701, a lever can be used. Similarly, instead of the knob 701, a spring-loaded release mechanism can actuate the deployable portion 204. In an alternative embodiment, the deployable portion 204 can be actuated with a magnetic system. In this configuration, the deployable portion 204 is fitted with a magnet (e.g., a permanent magnet or a ferromagnetic target). A complementary magnet (e.g., a permanent magnet or a electromagnet target) external to the body or patient is used to interact with the magnet on the deployable portion 204, such that an operator can open and close the deployable portion 204 by moving the external magnet about and in relation to the deployable portion 204.

The hinge arrangements for the opening/closing of the deployable portions 204 may be accomplished in a number of ways. In one embodiment, one or more of the deployable portions 204 transition between a closed and a number of open positions via a hinge arrangement. The hinge arrangement may include a hinge disposed within a wall of the tubular element 110, e.g., all or partially within the lumen 202, around a pivot point, on a circumference of the tubular element 110, e.g., a circumferential hinge, and/or on an exterior of the tubular element 110. Alternatively, the hinge arrangement may include at least one four-bar linkage.

In an alternative embodiment, the lumen 202 is kept clear by passing the links 704, 706 through a recess along or an aperture formed inside the tubular element 110 wall. In an alternative embodiment, the adjustment means 106 include electro-mechanical actuation of switches, operated by the surgeon or clinician, that drive one or more motors. The motors or actuators may be located either within the proximal end 114 (e.g., non-deployable portions) of the tubular element 110, or within the deployable portion 204. Alternatively, the deployable portion 204 can be moved via a pneumatic or fluidic actuator.

In an alternative embodiment, the hinge connecting the deployable portion 204 to the distal end 116 can include Shape Memory Alloy (SMA) materials with or without an assisted heating element. In one embodiment, using a material such as Nitinol (located within the lumen 202, tubular element 110 and/or the deployable portion 204), any deployable portion 204 can be closed at room temperature (e.g., 25° C.), and deploy at the temperature less than that expected within the body cavity (e.g., less than 37° C.). In an alternative embodiment, the assisted heating element can be controlled by the surgeon or clinician. The voltage for the assisted heating element can be transmitted along the tubular element 110 walls. The assisted heating element is used to place the SMA material into the deployable temperature range once within the body cavity; for example, increasing the voltage will increase the temperature of the SMA material, which transitions the deployable portion 204 to one or more of its open positions. Removing or decreasing the voltage (and hence the heat), makes the deployable portion 204 transition to its closed position.

Figure 6:
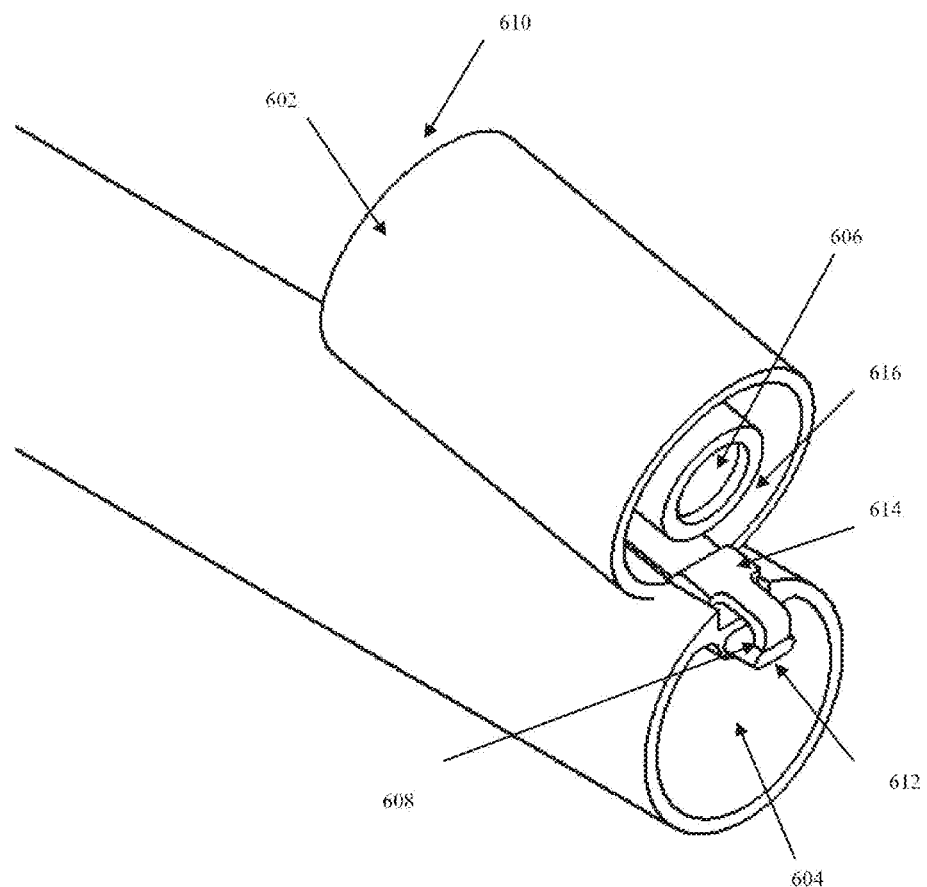
FIG. 6 depicts a schematic perspective close-up view of another embodiment of a tip section of a cannula assembly in one of its open positions, according to an embodiment of the present invention.

In one embodiment, as depicted in FIG. 6, the link 612 is a single element, e.g., a tape or rod, made of metal or other non-buckling configuration, which when pushed towards the distal end by the surgeon via operation of the knob 701, causes it to extend towards the distal end of the lumen 604. The extending pressure forces the hinge arrangement 608, 614 on the deployable portion 602 to flip and to rotate into one or more open positions, causing the formerly distal facing portion 610 to now face towards the proximal end. In this configuration, the imaging component 606 and illumination component 616 face the area of interest. The angle of opening of the deployable portion 602 may be adjusted by the amount of link 612 fed into the tubular element 110 through the rotation of the knob 701 or other structural adjustment mechanism. This arrangement allows for the image component 606 and illumination components 616 to occupy almost or all of the lumen 604 when closed, and to leave the lumen 604 substantially open and available for instrument insertion/operation and/or removal of both instruments and body samples when open. In addition, this arrangement protects any image or illumination components when closed, while allowing the same degree of triangulation by adjustment of either the opening angle for the deployable portion 602 and/or the image component 606 and illumination component 616. Similar hinge arrangements and adjustment means to those described herein may also be used.

Figure 8:
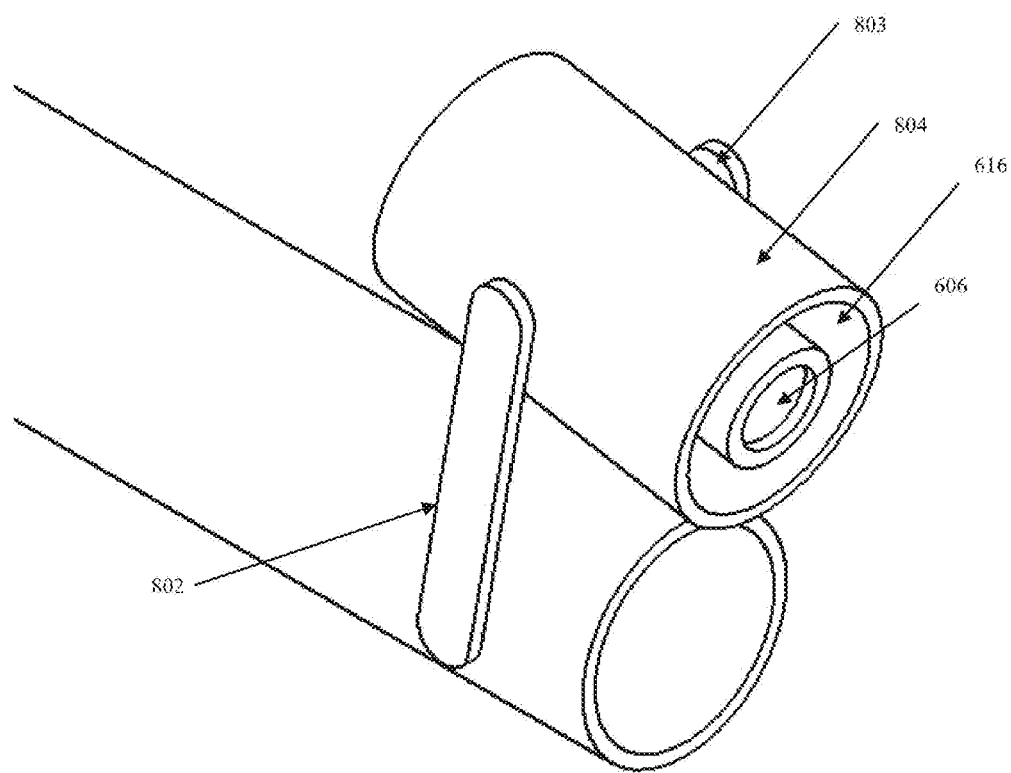
FIG. 8 depicts a schematic perspective close-up view of a tip section of a cannula assembly in one of its open positions, according to another embodiment of the present invention.

In an alternative embodiment, as depicted in FIG. 8, the hinge arrangement is a four-bar linkage with arms 802, 803 that are attached to a deployable portion 804. In this arrangement, the deployable portion 804 can be similarly actuated as described above. For example, one or more links passing internally through the wall of the tubular element 110 connect to the arms 802, 803. Rotation of the knob or a push of a push rod raises the deployable potion 804 above the tubular element 110. Imaging component 606 and illumination component 616 are housed in the deployable portion 804.

Figure 4:
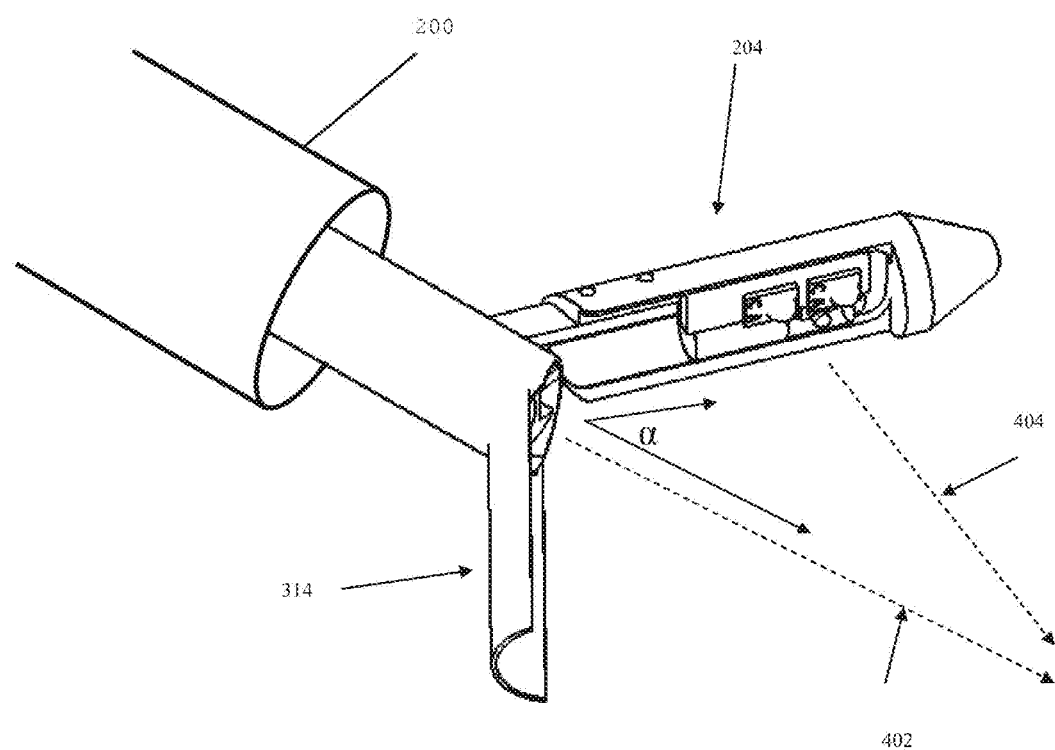
FIG. 4 depicts a close-up schematic perspective view of another embodiment of the tip section of a cannula assembly in one of its open positions, in accordance with an embodiment of the present invention.

In an alternative embodiment, as depicted in FIG. 4, the tubular element 110 can include a plurality of deployable portions, e.g., two or three deployable portions. For example, as shown in FIG. 4, one embodiment includes two deployable portions, one deployable portion 205 with electronic components (e.g., one or more image transmission components and/or one or more illumination components), the other deployable portion 314 without electronic components. Alternatively, both deployable portions 205, 314 can include electronic components. One or both of the deployable portions 205, 314 can open in response to user input. The number of deployable portions is only limited by the ability to divide the circumference of the tubular element 110, in either homogeneous or dissimilar sized portions. One or more such deployable portions may be formed, using any combination of the adjustment means discussed herein. This gives the surgeon or clinician additional freedom from cannula interference in the area where the surgery or operation is taking place.

In one embodiment, the deployable portion 204 containing electronic component is actuated with mechanical links, while the other deployable portion 314, with no electronic component, uses SMA means for deployment. This would allow the fine pointing/triangulation for the deployable portion 204 with electronic components, and a simpler, less precise adjustment mechanism for the other deployable portion 314. In another embodiment, a complementary set of electronics is housed in each deployable portion 204, 314, providing system redundancy selectable by the surgeon or operator. In another embodiment, the tubular element 110 can include three deployable portions, one containing image transmission components, the other containing illumination components, and the last one having no electronic component. Alternatively, at least one or more of an image transmission component and an illumination component can be disposed on each of the deployable portions.

The deployable portion(s) 204 of the tubular element 110 is configured to move from the closed position aligned with the tubular element 110 (i.e., at zero degrees) into an infinite number of open positions from zero to 180 degrees relative to the centerline axis defined by the tubular element 110. This provides the surgeon or operator with the ability to effectively "triangulate" one or more of the field of views of the image transmission component and the illumination component. As may be seen in FIG. 4, adjusting the angle α of the opening of the deployable portion 204 relative to the axis 402 of the tubular element 110, causes the direction of view 404, e.g., of the image transmission component or illumination component, to be adjusted without movement of the cannula. This allows the view to be changed slightly, without reverting to the need to move the cannula. During a procedure, moving the cannula may affect an instrument's position, vis-à-vis the organ or body structure being operated on. In use, the cannula may be rotated so that the image transmission component and the illumination component cover more fields of view. The rotation of the cannula can be tracked to keep the image in one orientation. In various embodiments, an accelerometer, an encoder (e.g., mechanical or optical), or other suitable feedback element disposed in the cannula assembly can communicate with control electronics in the video output of the image transmission component to rotate the image before it is displayed to the operator, in order to maintain the image in the same orientation. The feedback element may have a fixed reference point to indicate a preferred orientation, such as a vertical or up orientation. The fixed reference point of the feedback element corresponds to a particular reference point or orientation of the image transmission component. This may be the same orientation, such as an up orientation. Rotation of the cannula can be accomplished automatically without user-intervention or the rotation can be controlled by the operator. Within the image transmission component, well known and understood imaging features may be implemented, including electro-optic image stabilization and others.

A fail-safe design feature of the cannula assembly results from the hinge arrangement for the deployable portion(s) 204 being located at a point upstream of the distal end 116. The deployable portion 204 can be closed upon extraction of the cannula assembly through the force exerted on it during withdrawal through an external insertion cannula 200. In this configuration, the deployable portion 204 is moved to the closed position without operation of the adjustment means 106.

All or part of the distal end 116 of the tubular element 110 may be formed from an optically transparent material as a trocar, pointed tip, or any suitably shaped frontal form. In combination with a deployable or removable mirror occupying all or part of the interior volume of the lumen 202, the surgeon or operator would be able to see a forward view beyond the cannula assembly when the deployable portion 204 is at or near the closed position. In an alternative embodiment, a prism can be used in lieu of a mirror.

Figure 5A:
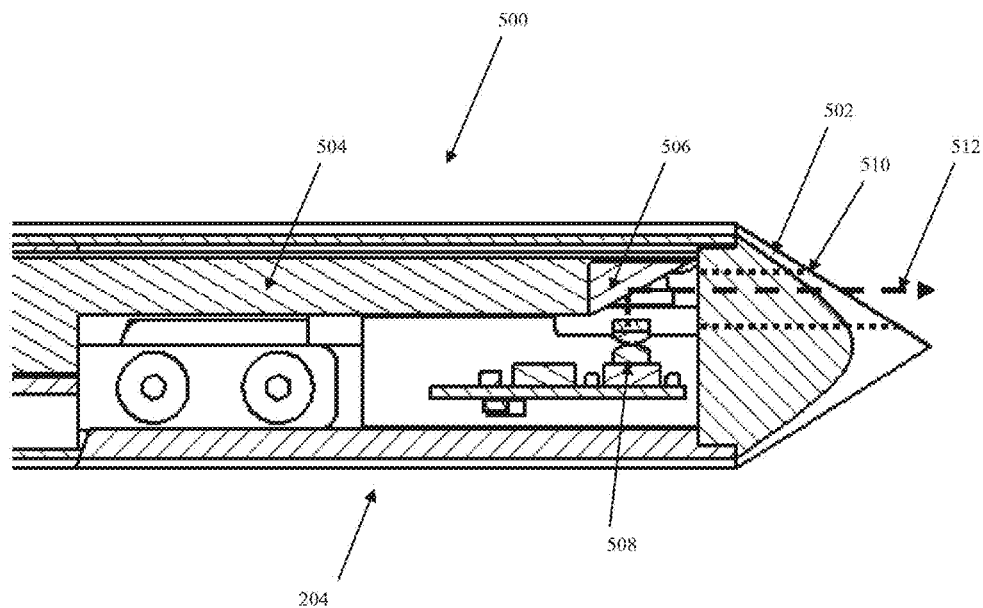
FIGS. 5A and 5B depict schematic cross-sectional and schematic partial sectional perspective views of a tip section of a cannula assembly in which an imaging component is configured for forward viewing while the cannula assembly is in the closed position, in accordance with an embodiment of the present invention.
Figure 5B:
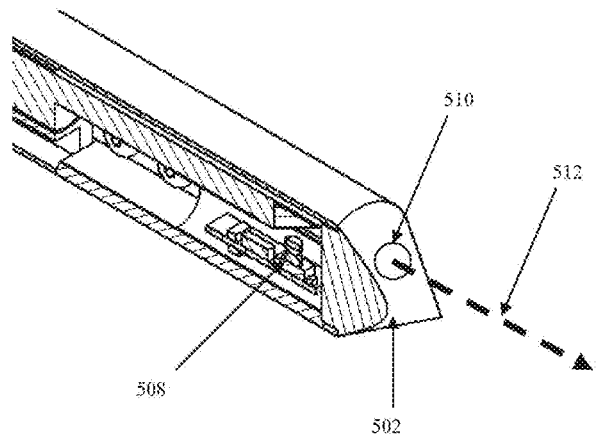

FIGS. 5A and 5B illustrate an embodiment of the cannula assembly 100 in which all or part of the trocar is made of optically transmissive or optically transparent materials. When the deployable portion 204 is in a closed position 500, the image transmission component 508 is capable of imaging through the distal end 502 of the cannula assembly via an optical path 512, which travels through a window 510, light pipe, or similar optically transmissive medium on the distal end 502.

Within the lumen, a mirror assembly, which can be one or more suitably reflective surfaces 506, can be placed at suitable angle(s) to permit the forward view. The reflective surface 506 forms a connection 504 (e.g., a rod) through the lumen 202 of the cannula assembly 100 to the proximal end 114, allowing the mirror assembly to be extracted once the deployable portion 204 is opened, if necessary.

Figures 9A, 9B:
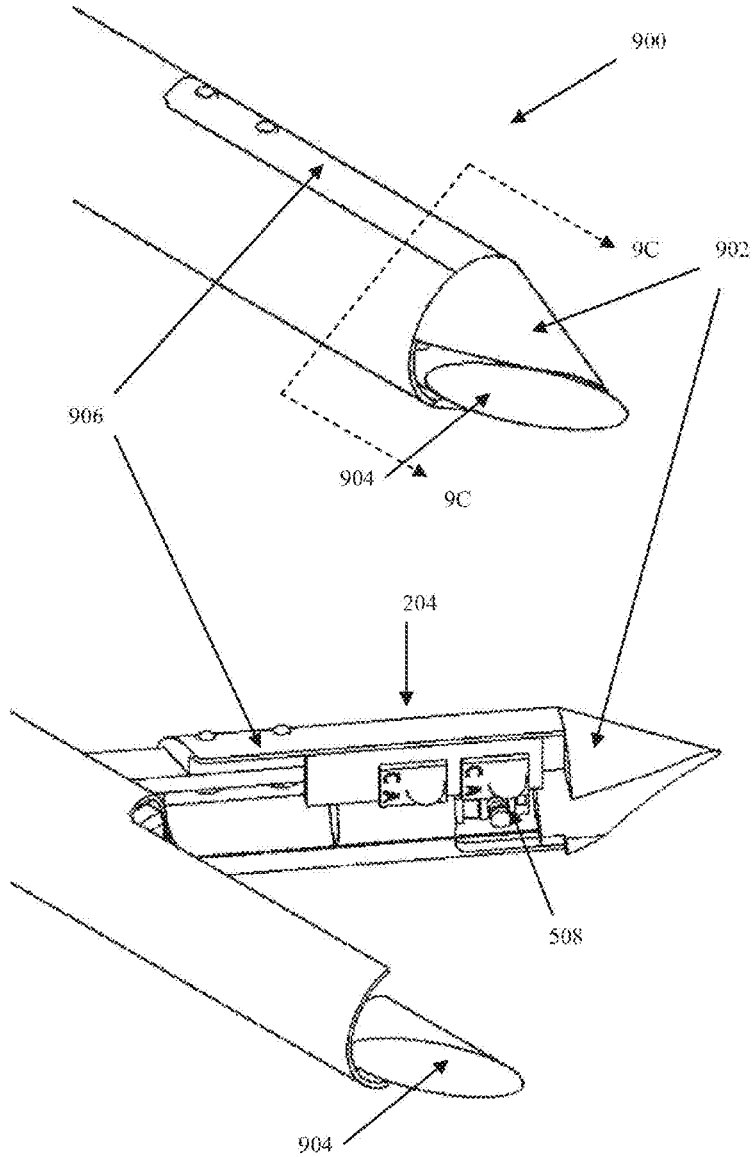
FIGS. 9A, 9B and 9C depict schematic perspective and schematic cross-sectional views of another tip embodiment of the apparatus with the capability of forward viewing while closed and having a removable trocar, according to an embodiment of the present invention.
Figure 9C:
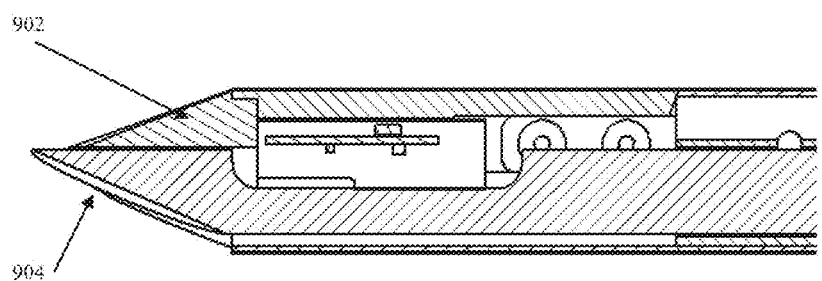

As depicted in FIGS. 9A, 9B and 9C, a cannula assembly 900 has the capability of forward viewing while the deployable portion 204 is in the closed position. In addition, the cannula assembly 900 can include a removable trocar. The distal end forms a combination of two portions. One is a deployable portion 204 (with external surface 902) and the other is a retractable portion 904. The deployable portion 204 may be made from any suitable material, while the retractable portion 904 is preferably made from an optically transmissive or optically transparent material. An optically transmissive or optically transparent material provides a window, that in combination with the mirror assembly inside the lumen (and similar to those described above), allows the imaging transmission component to view forward while the deployable portion 204 is in the closed position. Upon deployment, retractable portion 904 is retracted through the lumen by the surgeon or operator.

In one embodiment, additional illumination sources are placed within indentations in the external surface 904 facing the distal end. Such illumination sources would minimize reflections from the optically transmissive portions of the trocar coming back to the image transmission components. In an alternative embodiment, power for the illumination sources is provided by energy storage components placed within the cannula assembly, e.g., a battery in the handle, minimizing the interfacing to the rest of the cannula assembly. The surgeon can activate the illumination sources at the time of insertion of the cannula assembly. The illumination source may include any of the illumination sources described above. The energy storage component may be batteries or super-capacitors. The energy storage component can be attached to the rod 504 or can be connected to the illumination sources.

Figure 10A:
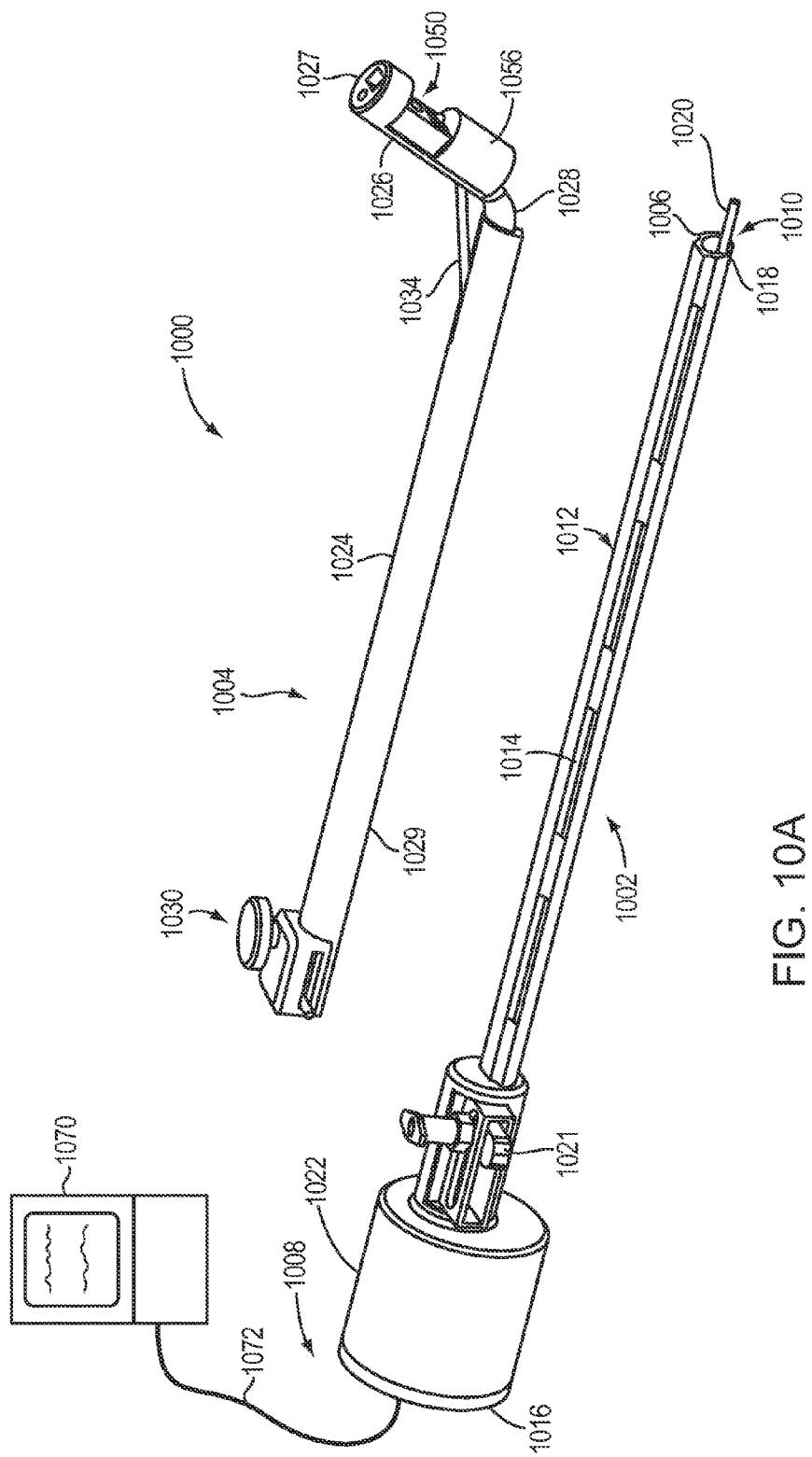
FIG. 10A depicts a schematic perspective view of a cannula assembly with a tubular element, a subassembly, and an ancillary electronics module in a separated state.
Figure 10B:
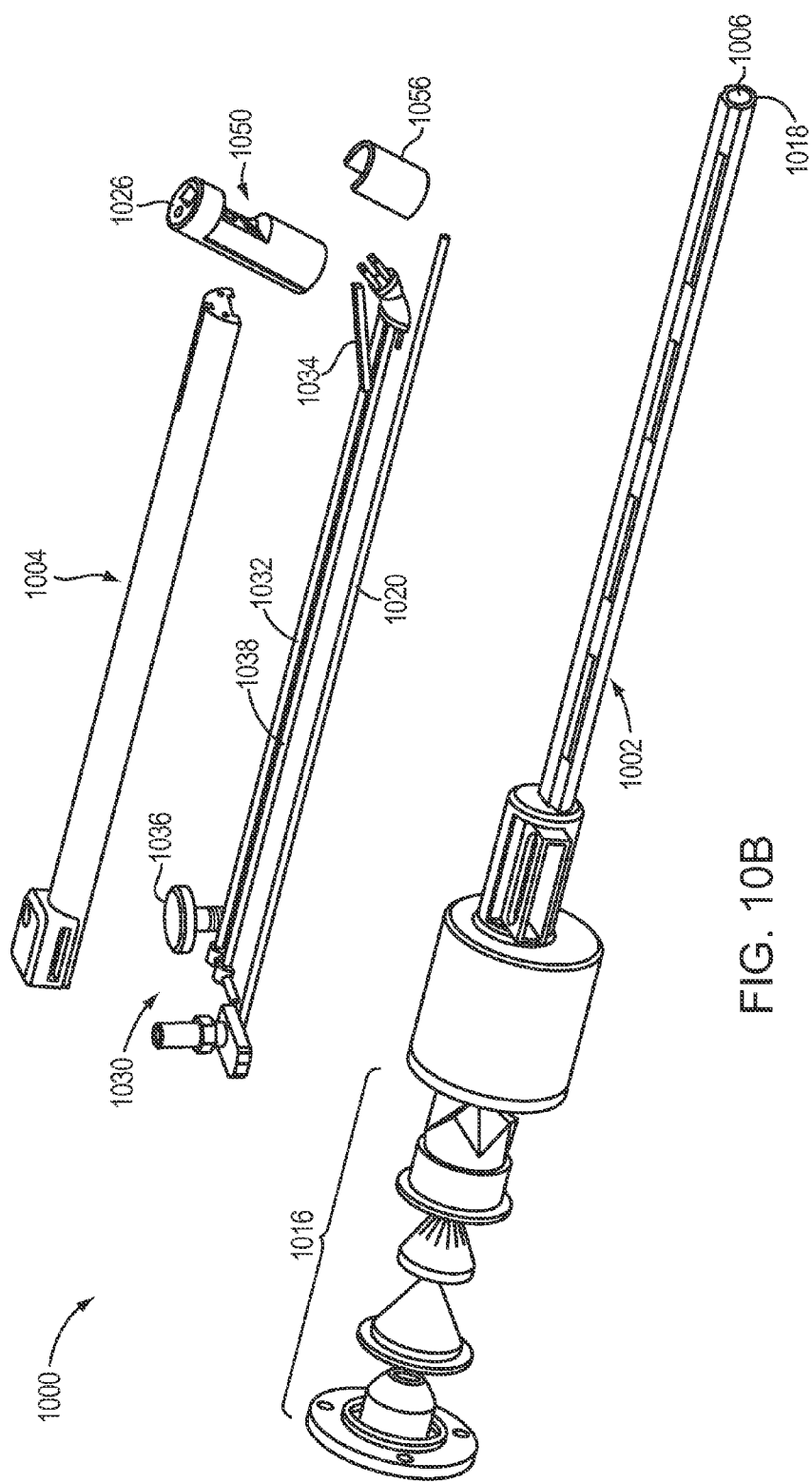
FIG. 10B depicts a schematic exploded perspective view of the tubular element and the subassembly of FIG. 10A.

In another embodiment, depicted in FIGS. 10A and 10B, a cannula assembly 1000 has two releasably connected components: a tubular element 1002 and a subassembly 1004. Releasably connecting the tubular element 1002 and subassembly 1004 has many benefits, such as allowing one component to be reusable while the other may be disposable. This is particularly useful when one component houses electronic components, which tend to be more costly to replace. In the embodiment depicted in FIG. 10A, the subassembly 1004 may contain many or all the electronics and be adapted for reuse following cleaning and sterilization, while the tubular element 1002 is provided sterile and is substantially without electronics, allowing for lower cost replacement as a disposable item.

The tubular element 1002 shares several similarities with the tubular element 110, including the formation of a lumen 1006 and definition of a proximal end 1008 and a distal end 1010 adapted to be inserted into a body. The lumen 1006 provides a passage for the travel of various objects, such as the introduction and removal of surgical instruments to an operation site and the removal of excised tissue. The lumen 1006 may be a variety of sizes, including having a diameter as small as 3 mm or less, or as large as 12 mm or larger. As the tubular element 1002 may be a single use component, it is feasible to manufacture tubular elements 1002 with various diameters of the lumen 1006 to accommodate various size instruments and tools for different procedures. Even with the various lumen 1006 diameters, these tubular elements 1002 can all be compatible and used interchangeably with the same subassembly 1004. The tubular element 1002 has a mating interface 1012 for receiving and securing the subassembly 1004. The mating interface 1012 may define one or more grooves 1014 adapted for receiving a corresponding surface (e.g., one or more longitudinal protrusions) of the subassembly, thereby allowing the subassembly 1004 to be slid (or snapped) onto and off of the tubular element 1002 while maintaining stability and structural integrity while the components are joined.

The tubular element 1002 may have a seal assembly 1016 at the proximal end 1008 to maintain a fluid seal within the lumen 1006, particularly following the introduction or removal of instruments. The seal 1016 may also provide a mechanism for maintaining an elevated gas pressure in the lumen 1006 for distension of a body cavity (e.g., the abdominal cavity), allowing space to perform surgical procedures, as is conventionally known.

At least one second lumen 1018 may be provided in the tubular element 1002, particularly for the passage of fluids. Such fluids may be introduced in a stream or pattern to remove contamination from components at the distal end 1010 (e.g., cameras, illumination sources) in situ, and may be specifically directed by a fitting at the distal end 1010. Enabling decontamination in situ reduces the frequency of removal of the cannula assembly 1000 for cleaning purposes, thereby reducing total operation time. Further, limiting removal and insertion reduces the opportunities for creating additional trauma and introducing contamination while the assembly 1000 is outside of the body. The second lumen 1018 can also be used for the removal of fluids in a bodily cavity, such as smoke and blood, which can obscure viewing of the cavity and associated tissue, and/or for the infusion of irrigation fluids to clean the cavity and associated tissue. Additionally, the second lumen 1018 may have a fitting (e.g., a female luer fitting) to facilitate the passage of fluids and that is sealable to prevent loss of insufflation pressure.

In some embodiments, a movable tube 1020 is disposed within the second lumen 1018. The movable tube 1020 can be rigid or flexible, depending on the application. To direct flow with a rigid tube, the movable tube 1020 can have an occluded distal tip and at least one side aperture. The movable tube 1020 can be oriented so fluid is selectively directed out of the side aperture (e.g., towards a camera or an illumination source). When the movable tube 1020 is flexible, the distal end thereof may be selectively curved to direct fluid out of the tip and/or other apertures. The flexible tube 1020 may be pre-curved so that when it exits the second lumen 1018 it regains its original shape (e.g., a shape-memory alloy, with or without heating), or may have some other control for manipulating the distal tip (e.g., a steering mechanism). Deployment of the movable tube 1020 may be controlled with a movable tube control 1021, such as a slider with or without a rotation feature.

The tubular element 1002 may further have a locking mechanism 1022 for selectively securing instruments within the lumen 1006. Various locking mechanisms 1022 are suitable, including a cam easily operable by a surgeon for providing a select amount of interference with objects (e.g., instruments) in the lumen 1006. Depending on the degree of interference of the closed cam with the lumen 1006, the objects may be substantially prevented from rotational and/or axial movement, or the cam may provide sufficient resistance to permit minor adjustments to the objects. Other locking mechanisms 1022 include use of a set screw and/or a linear or annular inflatable component that can be used to clamp or press against objects in the lumen 1006.

Figures 11, 12A:
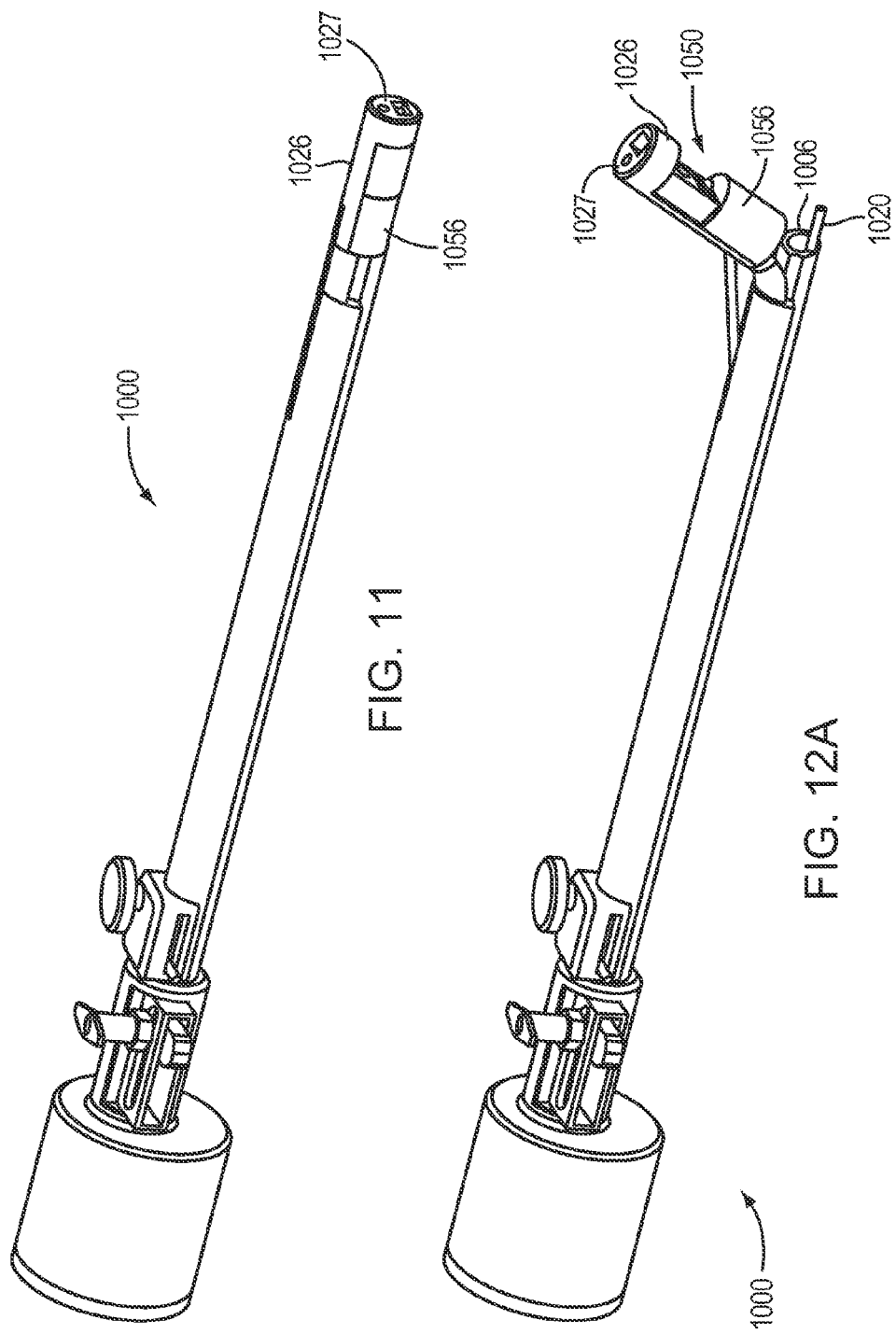
FIG. 11 depicts a schematic perspective view of the cannula assembly of FIG. 10A with a deployable element in a closed position.
FIGS. 12A-12C depict schematic perspective views of varying degrees of enlargement of the cannula assembly of FIG. 11 with the deployable element in an open position.
Figure 12B:
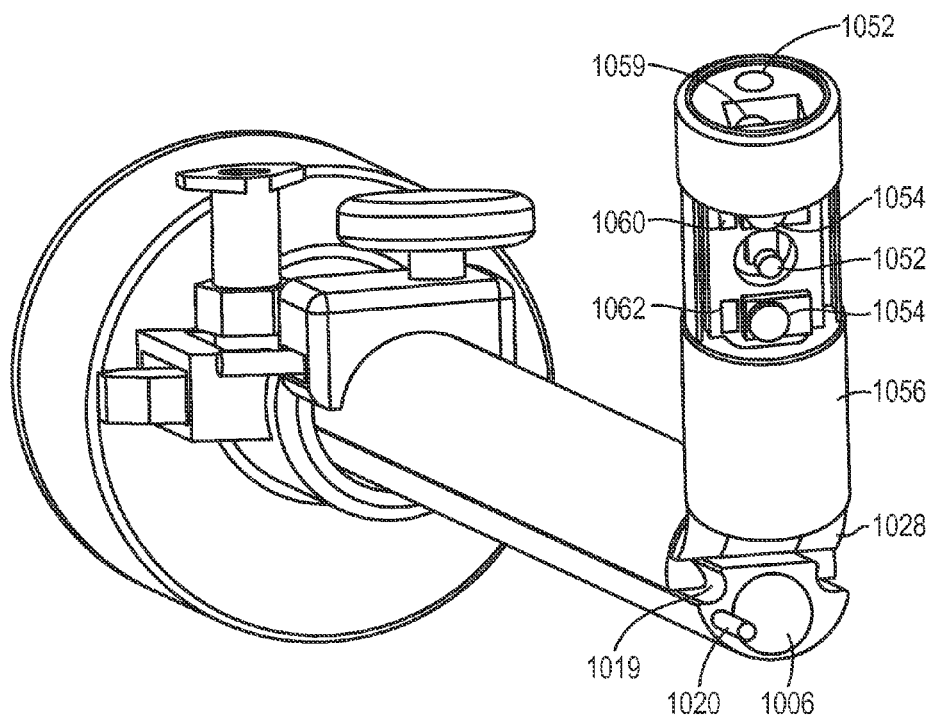
Figure 12C:
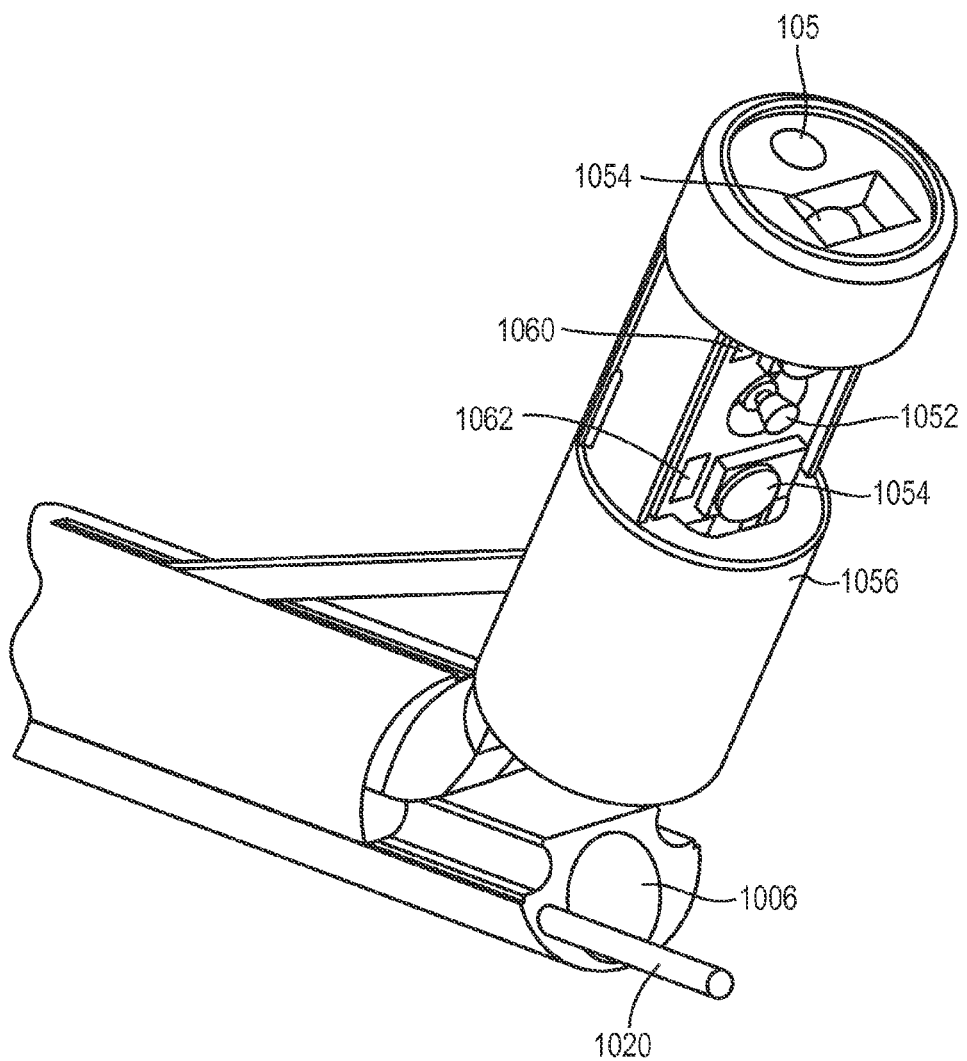

The subassembly 1004 has a body portion 1024 and a deployable element 1026 with a distal tip 1027. The body portion 1024 has a complementary mating interface 1029 relative to the mating interface 1012 on the tubular element 1004. The deployable element 1026 is connected to the body portion 1024 via a hinge 1028 or other mechanism providing at least one degree of freedom, enabling movement of the deployable element 1026 between a closed position (where the deployable element 1026 is substantially aligned with the body portion 1024; see FIG. 11) and an open position (where the deployable element 1026 is angled with respect to the body portion 1024; see FIGS. 12A-12C for partial opening). The hinge 1028 maintains the connection between the body portion 1024 and the deployable element 1026 in all positions (and thus the tubular element 1002), including any position between entirely open (e.g., up to 180°) and closed, and may be configured to maintain the deployable element 1026 in any position. The hinge 1028 may be spring loaded to bias the deployable element 1026 into the fully open position, staying closed or at any intermediate position using a latch or some other mechanical restraint, and may be forced to the closed position from the open position when the assembly 1000 is attempted to be removed from a body in the open position, due to compliance in the opening or biasing mechanism. When the subassembly 1004 is properly mounted to the tubular element 1002, the deployable element 1026 is disposed proximate the distal end 1010. In the closed position, the deployable element 1026 substantially obstructs the lumen 1006, while the deployable element 1026 does not substantially obstruct the lumen 1006 when in the open position.

Opening and closing may be achieved through the use of an actuating mechanism 1030 that may be similar to the adjustment means 106. The actuating mechanism 1030 can include an elevation control 1032 and a linkage 1034 connecting the elevation control 1034 to the deployable element 1026. A knob 1036 is coupled to the elevation control 1032, such that rotation causing movement of the elevation control 1032 causes the deployable element 1026 to be either raised or lowered. If the hinge 1028 is biased into the fully open position, the actuating mechanism 1030 may operate in opposition to the bias force and provide sufficient force, friction, or detents to allow the user to set the extent of deployment. As mentioned above, compliance in the actuating mechanism 1030 can permit fail-safe retraction from the body, even when in the fully or partially open position. A cover control 1038 may be provided for control of a movable element, as described in further detail below.

Figure 13:
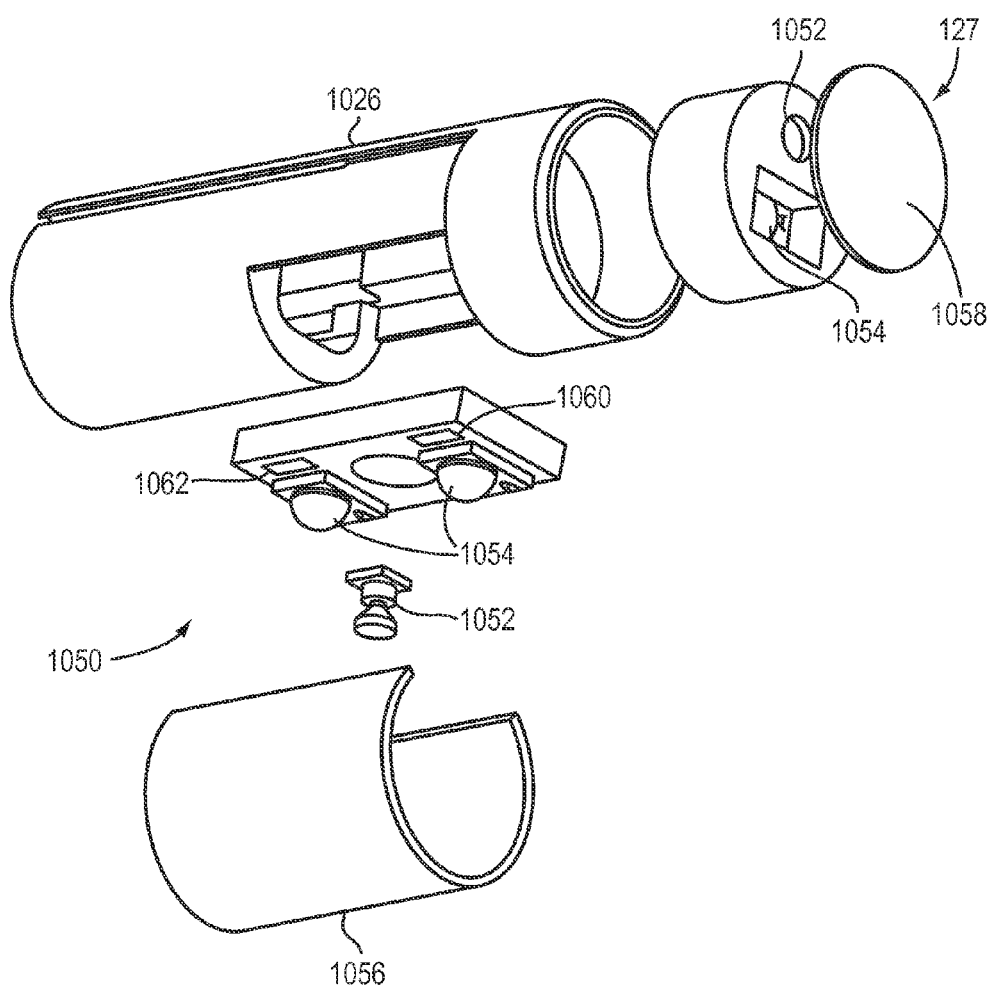
FIG. 13 depicts a schematic exploded perspective view of an electronic component for use in the cannula assembly of FIG. 10A.

The deployable element 1026 contains an electronic component 1050, depicted in FIG. 13. The electronic component 1050 may have at least one imaging device 1052 and at least one illumination source 1054 (e.g., a LED), similar to or the same as the image transmission components 304 and illumination sources 306 described above. One or more of the imaging devices 1052 and the illumination sources 1054 may be provided directed toward the distal tip 1027 to provide a forward view and/or illumination, especially when the deployable element 1026 is in the closed position. One or more of the imaging devices 1052 and the illumination sources 1054 may be directed radially outward from the deployable element 1026, providing a view and/or illumination in the closed and/or open positions. In some embodiments, the imaging devices 1052 and/or the illumination sources 1054 may be separately controllable with an additional degree of freedom (e.g., an imaging device 1052 is controlled to rotate about an axis distinct from the hinge axis to provide a pan view or to tilt for optimum field of view without movement of the deployable element 1026). A light guide may be used to direct illumination from an illumination source to a specific target as a means to reduce the number of illumination sources 1054 required for a particularly lighting application. The light guide may also be used to selectively control heating of surfaces that could potentially contact tissue.

A movable element 1056 may be provided on the deployable element 1026 to selectively cover at least one of the imaging device 1052 and the illumination source 1054, providing an additional layer of protection and helping prevent the lenses associated with these components from becoming prematurely contaminated and or otherwise obstructed (e.g., during insertion, removal, or handling). The cover control 1038 provides a linkage couple to the movable element 1056 for controlling movement of the movable element 1056. The movable element 1056 may be transparent to visible light to allow for operation of the imaging device 1052 and the illumination source 1054 even when the components are covered by the movable element 1056. Alternatively, the cover control 1038 may be programmed or configured so that the movable element 1056 is automatically moved depending on the environment and other operating conditions (e.g., moved down to uncover one or more electronic components when the deployable portion 1026 is moved to any open position). Any imaging device 1052 and/or illumination source 1054 in the distal tip 1027 may be protected with a cover 1058, which may be transparent. A heat source 1060 (along with temperature sensors) may be provided in the electronic component 1050 to sense and control the temperature of lenses on the imaging devices 1052 and/or the illumination sources 1054. The temperature can be controlled with a heating element or the like to reduce obscuring that can arise from condensation on the components in situ, and can help protect tissue from thermal damage if it is contacted by the components. The heat source 1060 may be any of a variety of heat sources, including an electric resistive heating element and/or an emitter of electromagnetic energy.

A multi-axis accelerometer 1062 may be provided on the deployable element 1026 to measure the orientation of the deployable element 1026 with respect to the direction of acceleration due to gravity. An ancillary electronics module 1070 (depicted in FIG. 10A) having a processor may be used to generate images with a selectable horizon based on inputs from the accelerometer 1062 and the imaging device 1052. This and other uses of an accelerometer are described above, and are applicable in this embodiment as well. The ancillary electronics module may be directly coupled to the cannula assembly 1000 (e.g., through electrical cables 1072 attached to the proximal end 1008 and conductors for conveying power and control signals within the assembly 1000), or may communicate via a wireless signal allowing for remote processing and viewing. Exemplary applications include a tablet computer or other mobile computing interface providing both the processing power and interface for viewing without the need for a hard wired connection. An additional multi-axis accelerometer 1062 may be located on the tubular element 1002. The use of multiple accelerometers 1062 in this manner enables the ancillary electronics module to determine an angle of deployment of the deployable element 1026 with respect to the tubular element 1002 based on inputs from the accelerometers 1062.

Controls for the electronic component 1050 may be mounted at the proximal end 1008 where they are easily accessible by the user. Controls can include magnification controls that adjust the magnification of the imaging devices 1052 for more precise imaging. Zooming can be accomplished by various methods, including electronically processing a digital image signal in the ancillary electronics module 1070 and/or using a mechanical optical lens mechanism. Other controls include operation of individual components (e.g., panning or tilting of the imaging device 1052 relative to the deployable portion 1026) and initiating and stopping recording of still images and video sequences in a digital memory of the ancillary electronic module 1070.

The assembly 1000 enables a reduction in the number of access ports typically required to perform common laparoscopic procedures by combining the electronic component 1050 with the tubular component 1002 having the lumen 1006. Additionally, the assembly 1000 has a tubular configuration when the deployable element 1026 is in the closed position that is compatible with standard sized access ports, and also serves to protect certain electronics (e.g., radial facing imaging devices 1052 and illumination sources 1054) from contamination during insertion or withdrawal. The forward facing view (e.g., as provided by the imaging device 1052 in the distal tip 1027) provides visualization of the pathway during insertion to help prevent tissue damage. Combined with at least one other imaging device 1052 facing radially, it is possible for a single surgeon to keep constant view of instrument tip placement, potentially reducing the risk of accidents while providing for a less stressful and faster procedure. The imaging devices 1052 on the deployable element 1026 can nearly replicate the viewing angle of open procedures and allow for rotation to view additional port placement.

During an operating procedure, the assembly 1000 is inserted into a body cavity. In embodiments with a forward facing imaging device 1052, the user may more accurately direct the assembly 1000 to a desired operating site based on the visual feedback. Once this site is reached, the deployable element 1026 is actuated to move from the closed position to an open position. With the deployable element 1026 open, any imaging devices 1052 or illumination sources 1054 facing radially outward from the deployable element 1026 may be focused on the operating site, thereby providing an image and/or illumination. If the accelerometer 1062 is included, the image may have a selectable horizon or be automatically adjusted to a predefined orientation following processing in the ancillary electronics module 1070. If two accelerometers 1062 are used, the ancillary electronics module may also determine an angle of deployment of the deployable element 1026 with respect to the tubular element 1002. The movement of the deployable element 1026 may substantially clear the lumen 1006 from obstructions, thereby allowing for the insertion of one or more instruments through the lumen 1006 to the operating site in the body cavity. To facilitate a surgical procedure, the instruments may be locked in position while in the lumen 1006. Once the surgical procedure is complete, the instruments and the assembly 1000 are removed from the patient's body, either separately or together. The tubular element 1002 is then separated from the subassembly 1004, allowing for proper disposal of the tubular element 1002 while the subassembly 1004 is cleaned and sterilized to be releasably attached to a new tubular element 1002 for use in a future procedure.

Various embodiments and features of the present invention have been described in detail with a certain degree of particularity. The utilities thereof can be appreciated by those skilled in the art. It should be emphasized that the above-described embodiments of the present invention merely describe possible examples of the implementations to set forth a clear understanding of the principles of the invention, and that numerous changes, variations, and modifications can be made to the embodiments described herein without departing from the spirit and scope of principles of the invention. Also, such variations and modifications are intended to be included herein within the scope of the present invention, as set forth in the appended claims. The scope of the present invention is defined by the appended claims, rather than the forgoing description of embodiments. Accordingly, what is desired to be secured by Letters Patent is the invention as defined and differentiated in the following claims, and all equivalents

The invention claimed is:

1. A cannula assembly comprising:
a tubular element forming a first lumen, the tubular element having a proximal end and a distal end adapted to be inserted into a body cavity;
a subassembly releasably attached to the tubular element, the subassembly comprising a deployable element disposed proximate the distal end of the tubular element, wherein the deployable element is adapted for movement between a closed position which substantially obstructs the first lumen and an open position which does not substantially obstruct the first lumen, wherein the deployable element remains coupled to the tubular element in the closed and open positions, and wherein at least one of the subassembly and the tubular element comprises at least two multi-axis accelerometers;
an electronic component coupled to the deployable element, wherein the electronic component comprises at least one imaging device and at least one illumination source, and wherein the subassembly, including the deployable element and the electronic component, are releasable from the tubular element; and
an ancillary electronics module comprising a processor adapted to generate images with a selectable horizon based on inputs from the multi-axis accelerometers and the imaging device, wherein the ancillary electronics module is adapted to determine an angle of deployment of the deployable element with respect to the tubular element based upon inputs from the multi-axis accelerometers.

2. The cannula assembly of claim 1, wherein the tubular element comprises a proximal sealing element adapted to maintain a fluid seal within the first lumen.

3. The cannula assembly of claim 1 further comprising a second lumen adapted for the passage of fluids.

4. The cannula assembly of claim 3, wherein the second lumen is disposed within the tubular element.

5. The cannula assembly of claim 3 further comprising a movable tube having a flexible distal end disposed within the second lumen.

6. The cannula assembly of claim 3 further comprising a movable tube having an occluded distal tip forming at least one side aperture disposed within the second lumen.

7. The cannula assembly of claim 1, wherein the subassembly is adapted to be cleaned, sterilized, and reused.

8. The cannula assembly of claim 1, wherein the electronic component further comprises a heat source.

9. The cannula assembly of claim 8, wherein the heat source is selected from the group consisting of an electric resistive heating element, an emitter of electromagnetic energy, and combinations thereof.

10. The cannula assembly of claim 1, wherein at least one of the imaging device and the illumination source is adapted to be operable in the closed position.

11. The cannula assembly of claim 1, wherein at least one of the imaging device and the illumination source is adapted to be operable in the open position.

12. The cannula assembly of claim 1, wherein the deployable element further comprises a hinge.

13. The cannula assembly of claim 12, wherein the hinge is adapted for movement from the open position to the closed position when the cannula assembly is being removed from a body in the open position.

14. The cannula assembly of claim 12, wherein the hinge is adapted to maintain the deployable element in a defined position.

15. The cannula assembly of claim 1, wherein the deployable element further comprises a movable element adapted to selectively cover at least one of the imaging device and the illumination source.

16. The cannula assembly of claim 15 further comprising a linkage coupled to the movable element adapted to control movement of the movable element.

17. The cannula assembly of claim 15, wherein the movable element is transparent to visible light.

18. The cannula assembly of claim 1 further comprising a controllable locking mechanism adapted to maintain positioning of a tool disposed within the first lumen.

19. A method of using a cannula assembly comprising:
inserting a tubular element forming a first lumen and a subassembly releasably attached to the tubular element into a body cavity, wherein the tubular element has a proximal end and a distal end;
actuating a substantially cylindrical deployable element of the subassembly from a closed position substantially obstructing the lumen to an open position, wherein an electronic component mounted to the deployable element comprises at least one imaging device for providing a forward view during insertion;
receiving inputs from at least two multi-axis accelerometers;
processing the inputs with an ancillary electronics module to determine an angle of deployment of the deployable element with respect to the tubular element;
inserting an instrument into the lumen for performing a surgical procedure; and
removing the tubular element and the subassembly from the body cavity.

20. The method of claim 19 further comprising locking the instrument in the lumen.

21. The method of claim 19, wherein the electronic component further comprises at least one radially facing imaging device and at least one radially facing illumination source.

22. The method of claim 19 further comprising:
processing inputs from at least one multi-axis accelerometer and the at least one imaging device with the ancillary electronics module to generate an image with a selectable horizon.

23. The method of claim 19 further comprising:
separating the tubular element from the subassembly; and
releasably attaching a new tubular element to the subassembly.

* * * * *